(12) United States Patent
Eikelboom et al.

(10) Patent No.: US 6,379,006 B1
(45) Date of Patent: Apr. 30, 2002

(54) STEREO SCANNING LASER OPHTHALMOSCOPE

(75) Inventors: Robert Henry Eikelboom, Brookdale; Fred Norbert Reinholz, Floreat; Paul Phillip Van Saarloos, Karrinyup, all of (AU)

(73) Assignee: The Lions Eye Institute of Western Australia Incorporated (AU)

( * ) Notice: Subject to any disclaimer, the term of this patent is extended or adjusted under 35 U.S.C. 154(b) by 0 days.

(21) Appl. No.: 09/555,242

(22) PCT Filed: Nov. 27, 1998

(86) PCT No.: PCT/AU98/00996
§ 371 Date: May 26, 2000
§ 102(e) Date: May 26, 2000

(87) PCT Pub. No.: WO99/27843
PCT Pub. Date: Jun. 10, 1999

(30) Foreign Application Priority Data

Nov. 28, 1997 (AU) .............................................. PP0621

(51) Int. Cl.[7] .............................................. A61B 3/12
(52) U.S. Cl. ...................................................... 351/221
(58) Field of Search ................................. 351/205, 206, 351/214, 216, 221, 210; 356/601, 606, 607, 608, 609, 484, 489; 250/559.22

(56) References Cited

U.S. PATENT DOCUMENTS

| 4,213,678 A | 7/1980 | Pomerantzeff et al. |
| 4,765,730 A | 8/1988 | Webb |

(List continued on next page.)

FOREIGN PATENT DOCUMENTS

| EP | 0821256 | 1/1998 |
| WO | 9730627 | 8/1997 |

*Primary Examiner*—George Manuel
(74) *Attorney, Agent, or Firm*—Baker Botts LLP (57) ABSTRACT

The present invention provides an apparatus for producing an image of a surface, including a laser source for producing a beam of light, beam modifying means for modifying the properties of the beam, beam splitting means for splitting the beam, focusing means for focusing the beam, first and second scanning means for scanning the beam in first and second different directions, stereo base producing means for obtaining stereoscopic information concerning the surface by impinging the beam onto the surface from two different positions, and reflecting means, wherein a beam from the laser source may be directing along an input path including being modified with the modifying means and split by the beam splitting means, directed onto the first scanning means to scan the beam in the first direction, directed through the second scanning means to scan the beam in the second direction, directed through the stereo base producing means, and then directed off the reflecting means and onto the surface, whereby reflected light from the surface traverses an output path identical to the input path, towards the beam splitting means, and whereby some of the reflected light is directed towards the photodetecting means coupled to the signal processing means and display means to produce an image for viewing with visualizing means in real time. The present invention also provides a method for scanning a surface with a laser beam to thereby produce an image of the surface, including directing a laser beam along an input path including modifying and then splitting the laser beam, focusing the beam, scanning the beam in a first direction, scanning the beam in a second direction, directing the beam through stereo base producing means to provide stereoscopic information by impinging the beam onto the surface from two different positions, and reflecting the beam onto the surface, whereby reflected light from the surface traverses an output path identical to the input path, splitting the beam and directing a portion of the split beam towards photodetecting means coupled to signal processing means and display means, whereby a resultant image may be viewed with visualizing means in real time.

73 Claims, 3 Drawing Sheets

U.S. PATENT DOCUMENTS

| | | |
|---|---|---|
| 4,900,144 A | 2/1990 | Kobayashi |
| 5,071,246 A | 12/1991 | Blaha et al. |
| 5,170,276 A | 12/1992 | Zinser |
| 5,268,711 A | 12/1993 | Poxleitner et al. |
| 5,303,709 A | 4/1994 | Dreher et al. |
| 5,353,073 A * | 10/1994 | Kobayashi .................. 351/221 |
| 5,430,509 A | 7/1995 | Kobayashi |
| 5,537,162 A | 7/1996 | Hellmuth et al. |
| 5,847,805 A * | 12/1998 | Kohayakawa et al. ...... 351/210 |
| 6,151,127 A * | 11/2000 | Kempe ....................... 356/484 |

* cited by examiner

STEREO SCANNING LASER OPHTHALMOSCOPE

The present invention relates to a method and apparatus for the stereoscopic examination of the fundus of the eye. This invention has applications in the investigation and diagnosis of diseases that affect the posterior chamber of the eyeball. The invention will be described in reference to the above application, however, it is possible and envisioned that the apparatus and technique of the present invention may be used for stereoscopic imaging in other medical processes.

Visualisation of the ocular fundus can provide important information about the state of the eye and of the body. Knowledge regarding ocular and systemic diseases, such as glaucoma, macula degeneration, diabetes or hypertension can be gained from examination of the posterior pole of the eye. In the past, imagining of the ocular fundus has been performed through the use of an ophthalmoscope, in which a direct view of the retina may be obtained. Other methods include the use of fundus cameras to obtain photographic images. However, these techniques usually require the use of mydriatic dilating drugs. The amount of light required to illuminate the fundus may also be uncomfortable for the patient.

Recent developments have resulted in the emergence of a new imaging tool for the ophthalmologist, in which an image of the eye may be observed in real-time and captured on a television monitor or screen, during procedures such as fluoreacein angiography. This instrument, known as a scanning laser ophthalmoscope (SLO), first described in U.S. Pat. No. 4,213,678, is currently used to produce representations of the ocular fundus in two dimensions. U.S. Pat. Nos. 4,765,730, 5,268,711 and 5,430,509 describe different embodiments of the scanning laser ophthalmoscope. All utilise a laser beam or light source that is directed through the pupil and onto the retina by way of two, directional, scanning mechanisms. The light from the laser is reflected off the retinal wall towards a photosensitive detection device. Electro-optical circuitry is employed to convert the light into synchronized signals, so that it is possible to display an image of the fundus on a television screen or monitor.

U.S. Pat. No. 5,430,509 describes a different embodiment of the scanning laser ophthalmoscope in which three or more scanning mechanisms are employed to develop a video image of the fundus. Scanning occurs in three directions, horizontal, vertical and in the direction of the optical axis. The inventors suggest that the use of three scanning devices, each with a different scanning frequency, will reduce the demands and wear on the scanner's bearings. However, despite the three scanning mechanisms, only a two dimensional image can be reconstructed on screen in real time.

The prior SLO technology described herein above does not permit stereoscopic viewing of the ocular fundus. Nevertheless, the optic disc region and retinal layers have three dimensional structure. Stereoscopic images of the ocular fundus can impart valuable information that cannot otherwise be derived from a two dimensional representation, especially in relation to the diagnosis of glaucoma. Efforts have therefore been made to create a device capable of producing three dimensional fundus images, while improving on the contrast and resolution of conventional SLO images.

Frambach, Dacey & Sadun (1992, 1993) describe a method of producing a three dimensional fundus picture during fluorescein angiography, using a modified SLO. To obtain stereoscopic data the SLO was manually moved from side to side during angiogram proceedings, much like a fundus camera is moved to enable viewing from two different positions. Individual frames from the video tape were chosen from left and right perspectives to provide a three dimensional image. An alternative approach employed by the authors involved the use of a modified Allen separator. A piece of flat glass was attached to an extended rod, coupled to the Allen separator, so that the glass was interposed between the eye and the SLO. The glass was then rapidly rotated to provide the left and right perspectives. The resulting frames were digitized by computer and viewed directly on a video screen. Superimposed images were formed by breaking a stereo pair down into corresponding fields and recombining them to form a single frame. LCD glasses were then used to view the left and right fields with the corresponding eye.

Frambach et al (1993) illustrate that achieving a stereoscopic image from a conventional scanning laser ophthalmoscope is possible. However, the methods involved exhibit a number of disadvantages. Frambach et al's first method of shifting the SLO involved awkward and confusing adjustments, resulting in poor stereoscopic image quality. In the second method, interference due to unwanted back reflections from the Allen separator would hinder in the transmission of stereoscopic information. Unwanted scattered light would impinge on the photodetecting element, causing a decrease in the contrast and resolution of the images.

Improvements in SLO image resolution and contrast are possible if the detector receives light only from the plane of interest and not scattered light from the media of the eye. A scanning laser ophthalmoscope that could provide high resolution, high contrast images of an ocular fundus was realised with the invention of the confocal scanning laser ophthalmoscope (cSLO), such as that described in U.S. Pat. Nos. 5,170,276 and 5,071,246. The confocal SLO utilises a pinhole or slit aperture to focus the light reflected from the fundus onto a photodetecting element. The aperture is located at a plane in which the opening is conjugate with the plane of the fundus of the eye. In this way, only the light reflected from the plane of interest impinges on the photodetecting element and any light scattered or reflected from out-of-focus planes is prevented from degrading the image.

A further technique to produce three dimensional images of the ocular fundus, known as scanning laser triangulation, is described by Milbocker & Reznichenko (1991). Triangulation is a method commonly used for measuring distances. Combined with a confocal aperture, this method involves synchronized scanning of a pixel of light across the fundus by way of two mirrors. The illumination and detection paths are arranged symmetrically and are defined by the two mirrors. The axial distance is measured by the displacement of the illuminated spot in the confocal plane, enabling calculation of the depth. (That is, the points above and below the 'average' position of the retinal wall). Disadvantages of this method include impractical computational speeds for clinical practice and an inflexible stereo base; large pupil and numerical apertures cannot be used with this technique.

Confocal scanning laser ophthalmoscopes are also currently used to provide three dimensional information concerning the ocular fundus. The confocal aperture of the cSLO allows the user to precisely focus on specific layers of the retina. By adjusting the focal plane of the aperture, images can be captured at different levels in the fundus, to reproduce desired depth characteristics. In this way a number of "optical sections" can be produced. A computer can then be used to extract depth information, through the process of "stacking" a selection of the optical sections taken at different levels of the retina. Information regarding the third dimension can therefore be interpolated.

Nevertheless, stereoscopic imaging via the method described is a time consuming process. A large number of images must be acquired at different focal planes. Interference from patient head and eye movement is likely to influence the resultant three dimensional image. Computer processing times must also be taken into account. These factors make confocal sectioning impractical in a clinical setting, where real time images are required for fast diagnosis or treatment.

U.S. Pat. No. 4,900,144 (also see Optics Communications: 87(1,2): 9-14) describes a scanning laser ophthalmoscope that utilises an alternative confocal focusing arrangement. The invention is capable of producing a three dimensional representation of an object that displays multiple reflectivity characteristics (such as the ocular fundus) through a method slightly different from the conventional confocal depth production described above. This US patent teaches the use of two separate confocal slit apertures and photodetecting units. The detection slits are orientated parallel to the direction in which the light, reflected from fundus, is scanned. However, both slits are slightly displaced from the normal position: the apertures are not conjugate with the fundus of the eye. One is positioned slightly to the front of the conjugate plane, while the other is placed to the rear. Because of the positioning of the confocal apertures, the output signals from the photodetectors vary in intensity according to the unevenness of the fundus. The resultant output signals are processed electronically by division calculations, detailed in U.S. Pat. No. 4,900,144, to obtain a three dimensional profile. The resultant real-time image displays the topography of the fundus through different shade levels, reflecting different retinal depth levels.

Software may also be used to create three dimensional graphic patterns. However, as in the above mentioned case, this method requires a high level of computer power to construct the three dimensional image. An increase in computer processing time is the inevitable result. It also relies on the incorrect assumption of homogeneity of the retina structures.

The above methods make use of the depth discrimination property, axial resolution, of the confocal system. Unlike the lateral resolution, the axial resolution is strongly limited by two factors. Firstly, the shape and size of the laser light focus which is scanned over the retina may suffer from deformations and distortions, particularly in the direction of the optical axis. This is due to the limited useful numerical aperture of the eye and its' optical imperfections. Furthermore, the size of the detection pinhole or slit may constrain the axial resolution of a confocal SLO. Due to intensity limitations on the living eye it is necessary to provide a detector aperture size which is larger than the optimal confocal pinhole in order to maintain a sufficient signal to noise ratio. As a result of these two factors the axial resolution of a confocal system is typically thirty times less than the lateral resolution.

Accordingly, there remains a need to provide a scanning laser ophthalmoscope capable of displaying true stereopsis, which is not restricted by any of the aforementioned limitations.

It is therefore an object of the present invention to provide an improved method and apparatus for producing a high contrast, real time, three dimensional representation of a scanned object.

It is a further object of the present invention to provide such an apparatus and method with the use of an additional scanning mechanism to gain information about the third dimension.

According, therefore, to the present invention, there is provided an apparatus for producing an image of a surface, including:

a laser source for producing a beam of light, beam modifying means for modifying the properties of the beam, beam splitting means for splitting the beam, focusing means for focusing the beam, first and second scanning means for scanning the beam in first and second different directions, stereo base producing means for obtaining stereoscopic information concerning the surface by impinging the beam onto the surface from two different positions, and reflecting means, wherein a beam from the laser source may be directed along an input path including being modified with the modifying means and split by the beam splitting means, directed onto the first scanning means to scan the beam in the first direction, directed through the second scanning means to scan the beam in the second direction, directed through the stereo base producing means, and then directed off the reflecting means and onto the surface, whereby reflected light from the surface traverses an output path identical to the input path, towards the beam splitting means, and whereby some of the reflected light is directed towards the photodetecting means coupled to the signal processing means and display means to produce an image for viewing with visualising means in real time.

Preferably the apparatus further includes confocal aperture means whereby the some of the reflected light is directed through the confocal aperture means towards the photodetecting means. The confocal aperture means may include a slit, diaphragm or a pinhole.

Preferably the apparatus includes beam guiding-means for guiding the beam before the beam is directed through the second scanning means, and preferably the beam modifying means includes a beam expander and/or a pinhole aperture.

Thus, although a beam guiding means is unnecessary in some configurations, it may be desirable in certain embodiments.

Preferably the apparatus includes a plurality of mirrors for directing the beam onto the first scanning means.

Thus, although a single mirror and/or lens may be employed, preferably the apparatus includes a plurality of such mirrors and/or lenses.

Preferably the first and second directions are perpendicular to one another, and more preferably one of the first and second directions is substantially horizontal and the other substantially vertical.

Preferably the surface is the ocular fundus.

The laser source is preferably a helium-neon laser source, a Ti:Sapphire laser source, an argon-ion laser source or a laser diode source. Preferably the laser source is one of a plurality laser sources.

The beam splitting means may be coated or non-coated.

Preferably the focusing means includes a plurality of mirrors and/or lenses.

Preferably the first scanning means includes a rotating polygon mirror. Alternatively the first scanning means includes an acousto-optic deflector or a mirror on a resonant scanner or on a galvanometer motor.

Preferably the second scanning means includes a mirror mounted on a scanning galvanometer motor, a resonant scanner or rotating polygon mirror.

Preferably the stereo base producing means is operable to obtain stereoscopic information by directing light onto the surface from a different position every alternate frame, and more preferably these two different positions are left and right positions. More preferably the stereo base producing means includes a pair of toggling mirrors for toggling every alternate frame to image the surface from two slightly different positions, with substantially overlapping imaging areas, to create a stereo pair.

Preferably the reflecting means is a large, curved mirror.

Preferably the photodetecting means includes a photomultiplier tube or an avalanche photodiode.

The signal processing means is preferably a computer with a video signal capture facility, while the display means is preferably a computer monitor or any other suitable display apparatus.

Preferably the visualising means is a pair of Liquid Crystal Display (LCD) goggles or a pair of goggles with a different coloured filter for each eye.

The present invention also provides a method for scanning a surface with a laser beam to thereby produce an image of the surface, including directing a laser beam along an input path including:

1) modifying and then splitting the laser beam,
2) focusing the beam,
3) scanning the beam in a first direction,
4) scanning the beam in a second direction,
5) directing the beam through stereo base producing means to provide stereoscopic information by impinging the beam onto the surface from two different positions, and
6) reflecting the beam onto the surface, whereby reflected light from the surface traverses an output path identical to the input path, splitting the beam and directing a portion of the split beam towards photodetecting means coupled to signal processing means and display means, whereby a resultant image may be viewed with visualising means in real time.

The method preferably includes directing the portion of the split beam through a confocal aperture means towards photodetecting means. The confocal aperture means include a slit, diaphragm or a pinhole.

Preferably the method includes guiding the beam before scanning the beam in the second direction. The beam guiding is preferably by means of beam guiding means including a curved mirror.

Preferably the first and second directions are perpendicular to one another. More preferably one of the first and second directions is substantially horizontal and the other substantially vertical.

Preferably the surface is an ocular fundus.

Preferably the beam modifying is performed by beam modifying optics including a beam expander and a pinhole aperture.

Preferably the beam modifying optics include a plurality of mirrors and/or lenses.

Preferably the method includes providing the laser beam by means of laser source means including a helium-neon laser source, a Ti:Sapphire laser, an argon-ion laser, a frequency doubled Nd:YAG laser source, a frequency doubled laser diode, or a laser diode.

Preferably the scanning the beam in a first direction is by means of first scanning means including a rotating polygon mirror.

Alternatively the first scanning means includes an acousto-optic deflector or a galvanometer mirror or a spinning multifaceted mirror, with the number of facets being a factor of the numbers of lines in the video standard, or a resonant scanner.

Preferably the scanning the beam in a second direction is by means of second scanning means including a mirror mounted on a scanning galvanometer motor, a resonant scanner or rotating polygon mirror.

Preferably the stereo base producing means is operable to obtain stereoscopic information by directing light onto the surface from a different position every alternate frame or half frame.

The stereo base producing means preferably includes a pair of toggling mirrors for toggling every alternate frame to image the surface from two slightly different positions, with substantially overlapping imaging areas, to create a stereo pair. Alternatively, it may include a toggling mirror and be operable to obtain stereoscopic information by adjusting the phase of the first scanning means. The adjusting may be effected mechanically or electronically.

Preferably the two positions are left and right positions.

Preferably the reflecting the beam onto the surface is performed by means of reflecting means including a large, curved mirror.

Preferably the photodetecting means includes a photomultiplier tube or an avalanche photodiode.

Preferably the signal processing means is a computer with a video signal capture facility.

Preferably the display means is a computer monitor or any other suitable display apparatus.

Preferably the visualising means is a pair of LCD goggles or a pair of goggles with a different coloured filter for each eye.

The present invention also provides an apparatus for visualizing human or animal tissue including:

laser source means for producing a beam of substantially collimated light;

beam modifying means for modifying the beam and/or controlling characteristics of the beam;

beam splitting means for splitting the beam;

focusing means for focusing the beam;

first scanning means for scanning the beam in a first direction;

second scanning means for scanning the beam in a second direction substantially perpendicular to the first direction, whereby the beam can be converted into a raster pattern;

means for adjusting beam paths so scanned laser beam or beams approach tissue from different positions;

reflecting means for reflecting the raster pattern;

electro-optical means for controlling the rate of scanning in the first and second directions and the rate of depth scanning;

photodetecting means for detecting the light reflected from the tissue;

signal processing means for converting the signals into television lines;

display means for displaying an image; software means for converting the image into an interlaced image; and visualising means for viewing the image in three dimensions in real time.

Preferably the apparatus includes confocal aperture means for substantially eliminating scattered, unwanted light or out of focus light. The confocal aperture means is preferably a slit, diaphragm or pinhole.

Preferably the apparatus includes beam guiding means for guiding the beam onto the second scanning means. The beam guiding means preferably includes a curved mirror. Alternatively the beam guiding means may include lenses and/or mirrors.

Preferably the laser source means is a helium-neon laser source, a Ti:Sapphire laser source, an argon-ion laser source, a frequency doubled Nd:YAG laser source, a frequency doubled laser diode, a laser diode source or any other monochromatic light source.

Preferably the laser source means includes two or more laser sources.

Preferably the beam modifying means includes a beam expander and/or a pinhole.

Preferably the second focusing optics includes a plurality of mirrors and/or lenses.

Preferably the first scanning means includes an acousto-optic deflector or a resonant or galvanometer mirror or a spinning multifaceted mirror, with the number of facets being a factor of the numbers of lines in the video standard (e.g. 5 or 25 for PAL), or a resonant scanner.

Preferably the second scanning means includes a galvanometer mounted mirror, or a resonant scanner or a rotating polygon mirror.

Preferably the stereo base producing means is operable to provide stereoscopic information about the surface by directing light onto the surface from two different positions, alternating every alternate frame, and more preferably the stereo base producing means includes a pair of toggling mirrors that toggle every alternate frame to image the surface from slightly different positions, with substantially overlapping imaging areas, such that a stereo pair can be created.

Alternatively the one or both of the pair of toggling mirrors may be replaced by electronic circuitry that can vary the phase of the first scanning means, or a galvanometer for turning the whole first scanning means, a prism or glass plate or any other means that is capable of directing light onto the surface from disparate positions every alternate frame.

Preferably the reflecting means is a large, curved mirror.

Preferably the electro-optic means is a plurality of electric circuits with optical or electronic feedback on the scan position of the mirrors.

Preferably the photodetecting means includes a photo-multiplier tube, or an avalanche photodiode.

Preferably the signal processing means is a computer with a video signal capture facility.

Preferably the display means is a computer monitor or any other suitable display monitor. Preferably the software means is an image processing program that is capable of producing an interlaced image in real time.

Preferably the visualizing means includes a pair of LCD goggles or a pair of goggles with a different coloured filter for each eye.

The tissue may be ocular, which may be the fundus of an eye, in the optic nerve head region, or any other ocular feature of interest.

Preferably the first direction is substantially horizontal.

BRIEF DESCRIPTION OF THE DRAWINGS

In order that the invention be more fully ascertained, some preferred embodiments will be described, by way of example, with reference to the accompanying drawing in which.

Figure 1:
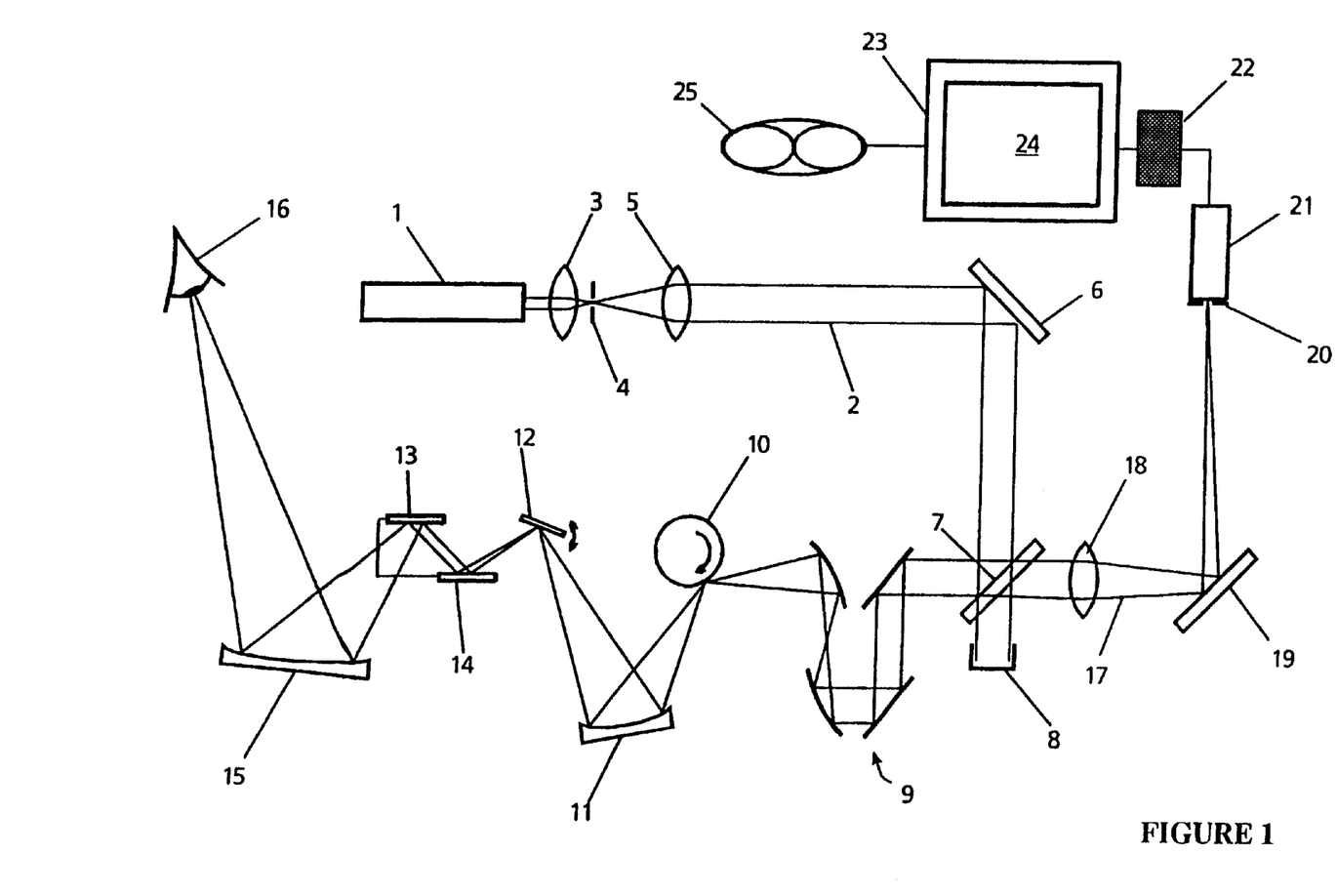
FIG. 1 is a schematic diagram of a first preferred embodiment of the present invention.

Referring to FIG. 1, a preferred embodiment of the present invention utilises a Helium-Neon laser source 1, or any other suitable source of substantially collimated light, which emits a laser beam 2. Alternatively, two or more laser sources may be utilised to produce beam 2. This beam is directed through a focusing system including beam expanders 3 and 5 (in the form of lenses), which expand the beam to a specified size, and a pinhole 4 between beam expanders 3 and 5. The beam 2 is then reflected from a mirror 6 towards beam splitting means in the form of beam splitter 7. Part of the light passes through the beam splitter 7 into a light trap 8. The rest of the light is reflected towards a number of focusing mirrors 9. Alternatively a lens or combination of lens and mirrors may be placed at this point. The focusing mirrors 9 guide the beam onto a resonant scanner or a rapidly rotating multiple facet mirror 10, which acts as a horizontal scanner, and subsequently onto a small curved mirror 11, which shapes the beam into a horizontal line. The beam travels to a vertical scanner 12, in this case a galvanometer controlled mirror, and is preferably directed onto a pair of toggling mirrors 13 and 14. These mirrors are positioned so that each directs the beam 2 onto the surface-to-be-imaged from two slightly different positions, with substantially overlapping imaging areas. They preferably toggle every alternate frame, such that visual information is received from the right and left perspectives in alternate frames. A second preferred embodiment would position toggling mirrors 13 and/or 14 before the horizontal scanning mechanism 10. Alternatively, the two toggling mirrors could be substituted with a single mirror that can change position preferably every second frame or half frame, or a galvanometer mounted prism or glass plate that is capable of imaging from the left and right perspective every half frame. Further embodiments include replacing toggling mirrors 13 or 14 with electronics that can vary the phase of the horizontal scanner or with a galvanometer that can turn the whole horizontal scanner.

The toggling mirrors 13 and 14, or one of the various alternatives, rapidly direct the beam through the pupil of eye 16 from two slightly different positions. The light, now a raster, is reflected off a large curved mirror 15 before entering the eye. The light that enters the eye through the pupil 16 passes through the eye's internal structure to reach the retina at the back of the fundus. The light is reflected off the retinal layers and travels to the exterior through the pupil. The reflected beam 17 traverses the same output path as the incident beam 2. Upon reaching beam splitter 7, most of the light continues through the beam splitter towards focusing means in the form of focusing optic 18. The reflected light is impinged off mirror 19 towards a confocal aperture 20, preferably a slit, although a pinhole configuration is also suitable. The beam then enters a photodetector 21, by preference a photomultiplier tube or an avalanche photodiode. The output of the photosensor is then preferably converted to a standard television signal pattern through signal processing means 22.

Figure 2:
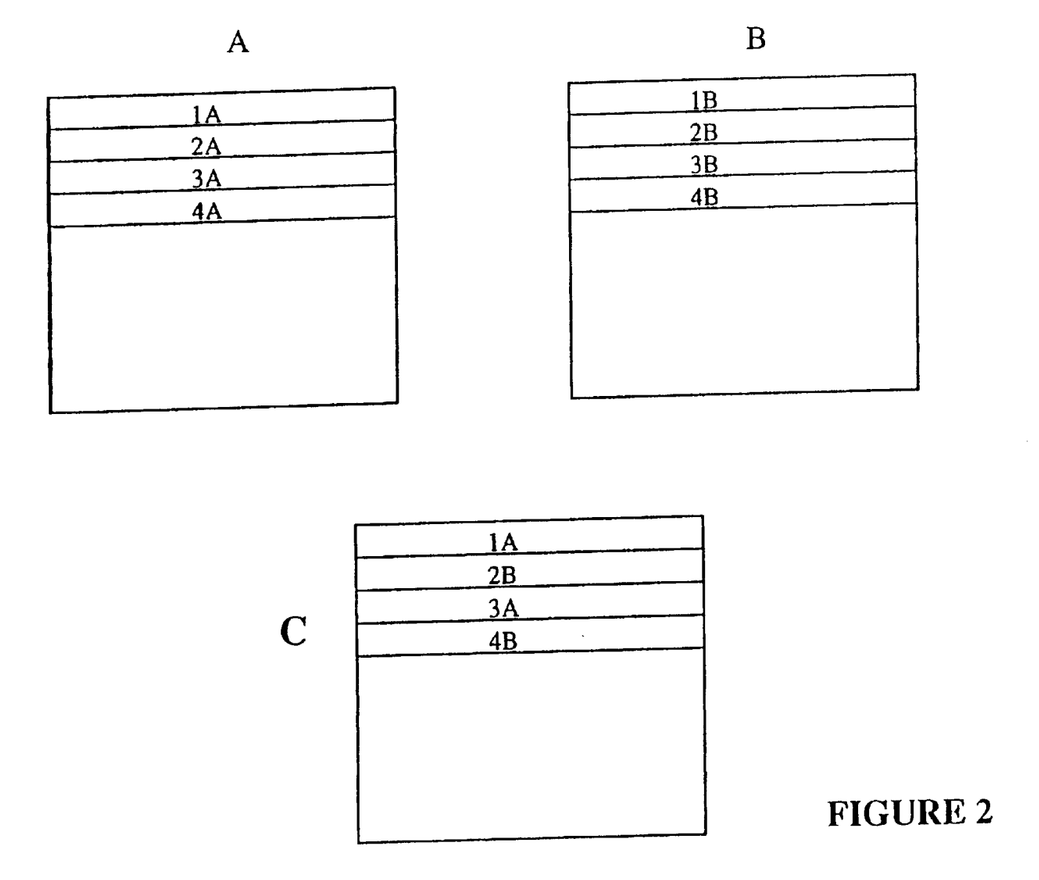
FIG. 2 illustrates the process of image production.

Electro-optic signals are received by an imaging board in computer 23 and appropriate electronic hardware and software converts the information sent from toggling mirrors 13 and 14 into first and second images. An interlaced image of half frames is then constructed on a monitor 24, preferably a computer monitor, in which every line or second line is captured from both images. Referring to FIG. 2, image A and image B, either of which may be the left or right image, are combined to form a single image C containing stereoscopic information. The top line of the interlaced image C is line 1A from, in this example, image A, while the next line down of image C is line 2B from image B. The process of capturing alternate lines from the two images continues until the completion of an interlaced image. A three dimensional view can then be perceived by an observer with the use of a pair of liquid crystal display (LCD) goggles 25 coupled to display means 24 (see FIG. 1). As the software writes the information from image A which may be, for example, the left image, the LCD goggles momentarily shutter the observer's right eye. A complementary process occurs with image B. In this way, the left eye views the left perspective, and the right eye views the right perspective, enabling the observer to detect a stereoscopic or three dimensional image of the ocular fundus in real time. Alternatively, an interlaced image can be written so that the lines from image A are one colour, (e.g. green) and the lines from image B are another (e.g. red). Wearing goggles with matching colour filters for each lens (e.g. red and green) allows each eye to perceive one image only, and thus view a stereoscopic image.

Figure 3:
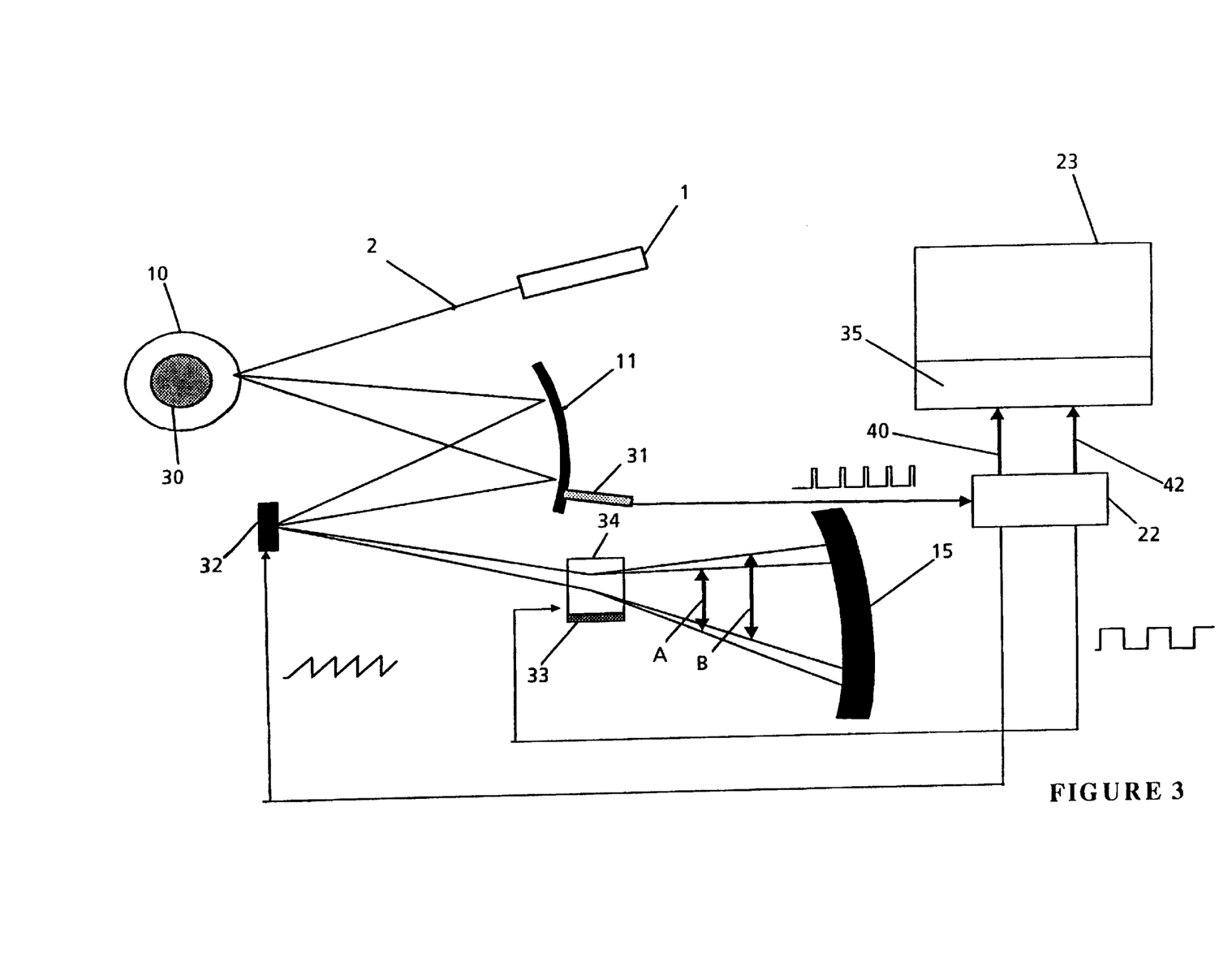
FIG. 3 is a schematic diagram illustrating an electrical configuration of one preferred embodiment of the present invention.

FIG. 3 illustrates the signal processing involved in controlling the scanning mechanisms. The focussing optics, beam splitter, photodetector and viewing apparatus have been omitted for simplicity. Corresponding reference numerals are used for like or corresponding parts from the several diagrams.

Electro-optic circuitry is employed to detect the beginning and the end of each raster and the end of each image frame. Laser source 1 produces a beam of monochromatic light 2 which is directed onto horizontal scanning mechanism 10. A driver 30, such as a 35000 RPM motor, drives the polygon mirror in circles to generate a horizontal line scan. Alternatively, a resonant scanner is driven in a sinusoidal pattern to generate the horizontal line scan. The line is reflected off mirror 11, and onto another mirror 32, which is driven in a sawtooth pattern perpendicular to the motion of the line. The action of 10 and 32 together produce a rectangular raster pattern. The timing of the start of the sawtooth pattern is set by the detection of the end or the start of the line at mirror 11. A detector 31 senses the end or start of the line, and this signal is conditioned into a sawtooth by signal processor 22. The signal processor 22 counts the number of lines in a raster and generates a frame synch. signal 40. A line synch. signal 42 is also generated. Both of these signals are sent to the SLO computer system 23. After the laser beam 2 has been converted into a raster, it is further deflected by the depth producing apparatus, which in this case is shown as prism 34. The signal processor 22 also sends a signal to the prism controller 33 to tell it when to move from one position (image A) to another (image B). The timing of this movement can be varied, but typically it is at the end of every frame or half frame. The signal processor typically sends a square wave to the controller. The laser beam is then impinged off mirror 15 and directed through the pupil onto the retina (not shown). The reflected beam traverses the output path described in FIG. 1 to the photodetector (not shown).

Signal processing means 22, coupled to the photodetector, sends electro-optic signals to imaging board 35, in computer 23, where appropriate hardware and software interprets them and constructs image A and image B as left and right perspectives. An interlaced image, is then created by specialized software and displayed on display means 24 (not shown) in real time. LCD goggles or other appropriate viewing means, can then be used to visualise the three dimensional interlaced image. The computer could also use the angle between the two images to calculate the real three dimensional shape.

Modification within the spirit and scope of the aforementioned invention may be readily effected by a person skilled in the art. Other embodiments would involve the use of a galvanometer mounted prism or glass plate in place of toggling mirrors to produce images from two different perspectives. Electronics that vary the phase of the horizontal scanner or a galvanometer that turns the whole horizontal scanner may also be utilised. It is to be understood, therefore, that this invention is not limited to the particular embodiments described by way of example hereinabove.

The claims defining the invention are as follows:

1. An apparatus for producing an image of a surface, including:
   a laser source for producing a beam of light,
   beam modifying means for modifying the properties of said beam,
   beam splitting means for splitting said beam,
   focussing means for focussing said beam,
   first and second scanning means for scanning said beam in first and second different directions,
   stereo base producing means for obtaining astereoscopic information concerning said surface by impinging said beam onto said surface from two different positions, and
   reflecting means, wherein a beam from said laser source may be directed along an input path including being modified with said modifying means and split by said beam splitting means, directed onto said first scanning means to scan said beam in said first direction, directed through said second scanning means to scan said beam in said second direction, directed through said stereo base producing means, and then directed off said reflecting means and onto said surface, whereby reflected light from said surface traverses an output path identical to the input path, towards said beam splitting means, and whereby some of the reflected light is directed towards said photodetecting means coupled to said signal processing means and display means to produce an image for viewing with visualizing means in real time.

2. An apparatus as claimed in claim 1, further including confocal aperture means whereby said some of said reflected light is directed through said confocal aperture means towards said photodetecting means.

3. An apparatus as claimed in claim 2, wherein said confocal aperture means includes a slit, diaphragm or a pinhole.

4. An apparatus as claimed in claim 1, wherein said apparatus includes beam guiding means for guiding said beam before said beam is directed through said second scanning means.

5. An apparatus as claimed in either claim 1, wherein said beam modifying means includes a beam expander and/or a pinhole aperture.

6. An apparatus as claimed in claim 5, wherein one of said first and second directions is substantially horizontal and the other substantially vertical.

7. An apparatus as claimed in claim 1, including a plurality of mirrors for directing said beam onto said first scanning means.

8. An apparatus as claimed in claim 1, wherein said first and second directions are perpendicular to one another.

9. An apparatus as claimed in claim 1, wherein said laser source is a helium-neon laser source, a Ti:Sapphire laser source, an argon-ion laser source, a frequency doubled Nd:YAG laser source, a frequency doubled laser diode, or a laser diode source.

10. An apparatus as claimed in claim 1, wherein said laser source is one of a plurality laser sources.

11. An apparatus as claimed in claim 1, wherein said focussing means includes a plurality of mirrors and/or lenses.

12. An apparatus as claimed in claim 1, wherein said first scanning means includes a rotating polygon mirror.

13. An apparatus as claimed in claim 1, wherein said first scanning means includes an acousto-optic deflector or a mirror on a resonant scanner or on a galvanometer motor, a resonant scanner or rotating polygon mirror.

14. An apparatus as claimed in claim 1, wherein said second scanning means includes a mirror mounted on a scanning galvanometer motor, a resonant scanner or a rotating polygon mirror.

15. An apparatus as claimed in claim 1, wherein said stereo base producing means is operable to obtain stereoscopic information by directing light onto the surface from a different position every alternate frame.

16. An apparatus as claimed in claim 1, wherein said two different positions from which said beam is impinged onto said surface are left and right positions.

17. An apparatus as claimed in claim 1, wherein said stereo base producing means includes a pair of toggling mirrors for toggling every alternate frame to image the surface from two slightly different positions, with substantially overlapping imaging areas, to create a stereo pair.

18. An apparatus as claimed in claim 1, wherein said reflecting means is a large, curved mirror.

19. An apparatus as claimed in claim 1, wherein said photodetecting means includes a photomultiplier tube or an avalanche photodiode.

20. An apparatus as claimed in claim 1, wherein said signal processing means is a computer with a video signal capture facility.

21. An apparatus as claimed in claim 1, wherein said display means is a computer monitor or any other suitable display apparatus.

22. An apparatus as claimed in claim 1, wherein said visualising means is a pair of Liquid Crystal Display goggles or a pair of goggles with a different coloured filter for each eye.

23. An apparatus as claimed in claim 1, wherein said surface is the ocular fundus.

24. An apparatus as claimed in claim 1, wherein said stereo base producing means includes a pair of toggling mirrors that toggle every alternate frame to image the surface from slightly different positions, with substantially overlapping imaging areas, such that a stereo pair can be created.

25. A method for scanning a surface with a laser beam to thereby produce an image of said surface, including directing a laser beam along an input path including:
1) modifying and then splitting said laser beam,
2) focussing said beam,
3) scanning said beam in a first direction,
4) scanning said beam in a second direction,
5) directing said beam through stereo base producing means to provide stereoscopic information by impinging said beam onto said surface from two different positions, and
6) reflecting said beam onto said surface, whereby reflected light from said surface traverses an output path identical to said input path,
splitting said beam and directing a portion of the split beam towards photodetecting means coupled to signal processing means and display means, whereby a resultant image may be viewed with visualising means in real time.

26. A method as claimed in claim 25, including directing said portion of said split beam through a confocal aperture means towards photodetecting means.

27. A method as claimed in claim 24, wherein said confocal aperture means includes a slit, diaphragm or a pinhole.

28. A method as claimed in claim 25, including guiding said beam before scanning said beam in said second direction.

29. A method as claimed in claim 28, wherein said beam guiding is by means of beam guiding means including a curved mirror.

30. A method as claimed in claim 25, wherein said first and second directions are perpendicular to one another.

31. A method as claimed in claim 30, wherein one of said first and second directions is substantially horizontal and the other substantially vertical.

32. A method as claimed in claim 25, wherein said surface is ganocular fundus.

33. A method as claimed in claim 25, wherein said beam modifying is performed by beam modifying optics including a beam expander and a pinhole aperture.

34. A method as claimed in claim 25, wherein said beam modifying is performed by modifying optics including a plurality of mirrors and/or lenses.

35. A method as claimed in claim 25, including providing said laser beam by means of laser source means including a helium-neon laser source, a Ti:Sapphire laser, an argon-ion laser, a frequency doubled Nd:YAG laser source, a frequency doubled laser diode, or a laser diode.

36. A method as claimed in claim 35, wherein said laser source means includes a plurality of laser sources.

37. A method as claimed in claim 25, wherein said scanning said beam in a first direction is by means of first scanning means including a rotating polygon mirror.

38. A method as claimed in claim 25, wherein said scanning said beam in a first direction is by means of first scanning means including an acousto-optic deflector or a galvanometer mirror or a spinning multifaceted mirror, with the number of facets being a factor of the numbers of lines in the video standard, or a resonant scanner.

39. A method as claimed in claim 25, wherein said scanning said beam in a second direction is by means of second scanning means including a mirror mounted on a scanning galvanometer motor, a resonant scanner or rotating polygon mirror.

40. A method as claimed in claim 25, wherein said stereo base producing means is operable to obtain stereoscopic information by directing light onto the surface from a different position every alternate frame or half frame.

41. A method as claimed in claim 25, wherein said stereo base producing means includes a pair of toggling mirrors for toggling every alternate frame to image the surface from two slightly different positions, with substantially overlapping imaging areas, to create a stereo pair.

42. A method as claimed in claim 25, wherein said stereo base producing means includes a toggling mirror and is operable to obtain stereoscopic information by adjusting the phase of said first scanning means.

43. A method as claimed in claim 42, wherein said adjusting is effected mechanically or electronically.

44. A method as claimed in claim 25, wherein said two different positions from which said beam is impinged onto said surface are left and right positions.

45. A method as claimed in claim 25, wherein said reflecting said beam onto said surface is performed by means of reflecting means including a large, curved mirror.

46. A method as claimed in claim 25, wherein said photodetecting means includes a photomultiplier tube or an avalanche photodiode.

47. A method as claimed in claim 25, wherein said signal processing means is a computer with a video signal capture facility.

48. A method as claimed in claim 25, wherein said display means is a computer monitor or any other suitable display apparatus.

49. A method as claimed in claim 25, wherein said visualising means is a pair of Liquid Crystal Display goggles or a pair of goggles with a different coloured filter for each eye.

50. An apparatus for visualizing human or animal tissue including:

laser source means for producing a beam of substantially collimated light;

beam modifying means for modifying said beam and/or controlling characteristics of said beam;

beam splitting means for splitting the beam;

focussing means for focussing the beam;

first scanning means for scanning said beam in a first direction;

second scanning means for scanning said beam in a second direction substantially perpendicular to said first direction, whereby said beam can be converted into a raster pattern;

means for adjusting beam paths so scanned laser beam or beams approach tissue from different positions;

reflecting means for reflecting said raster pattern;

electro-optical means for controlling the rate of scanning in said first and second directions and the rate of depth scanning;

photodetecting means for detecting the light reflected from said tissue;

signal processing means for converting the signals into television lines;

display means for displaying an image, software means for converting said image into an interlaced image; and visualising means for viewing said image in three dimensions in real time.

51. An apparatus as claimed in claim 50, including confocal aperture means for substantially eliminating scattered, unwanted light or out of focus light.

52. An apparatus as claimed in claim 51, wherein said confocal aperture means is a slit, diaphragm or pinhole.

53. An apparatus as claimed in claim 50, including beam guiding means for guiding said beam onto said second scanning means.

54. An apparatus as claimed in claim 53, wherein said beam guiding means includes a curved mirror, or lenses and/or mirrors.

55. An apparatus as claimed in claim 50, wherein said laser source means is a helium-neon laser source, a Ti:Sapphire laser source, an argon-ion laser source, a frequency doubled Nd:YAG laser source, a frequency doubled laser diode, a laser diode source or any other monochromatic light source.

56. An apparatus as claimed in claim 50, wherein said laser source means includes two or more laser sources.

57. An apparatus as claimed in claim 50, wherein said beam modifying means includes a beam expander and/or a pinhole.

58. An apparatus as claimed in claim 50, wherein said second focussing optics includes a plurality of mirrors and/or lenses.

59. An apparatus as claimed in claim 50, wherein said first scanning means includes an acousto-optic deflector, or a resonant or galvanometer mirror or a spinning multifaceted mirror, with the number of facets being a factor of the numbers of lines in the video standard, or a resonant scanner.

60. An apparatus as claimed in claim 50, wherein said second scanning means includes a galvanometer mounted mirror, or a resonant scanner or a rotating polygon mirror.

61. An apparatus as claimed in claim 50, wherein said stereo base producing means is operable to provide stereoscopic information about the surface by directing light onto the surface from two different positions, alternating every alternate frame.

62. An apparatus as claimed in claim 50, wherein said stereo base producing means includes electronic circuitry for varying the phase of the first scanning means, or a galvanometer for turning the whole first scanning means, and means for directing light onto the surface from disparate positions every alternate frame.

63. An apparatus as claimed in claim 50, wherein said reflecting means is a large, curved mirror.

64. An apparatus as claimed in claim 50, wherein said electro-optic means is a plurality of electric circuits with optical or electronic feedback on the scan position of the mirrors.

65. An apparatus as claimed in claim 50, wherein said photodetecting means includes a photomultiplier tube, or an avalanche photodiode.

66. An apparatus as claimed in claim 50, wherein said signal processing means is a computer with a video signal capture facility.

67. An apparatus as claimed in claim 50, wherein said display means is a computer monitor or any other suitable display monitor.

68. An apparatus as claimed in claim 50, wherein said software means is an image processing program for producing an interlaced image in real time.

69. An apparatus as claimed in claim 50, wherein said visualizing means includes a pair of Liquid Crystal Display goggles or a pair of goggles with a different coloured filter for each eye.

70. An apparatus as claimed in claim 50, wherein said tissue is ocular.

71. An apparatus as claimed in claim 50, wherein said ocular tissue is the fundus of an eye.

72. An apparatus as claimed in claim 50, wherein said tissue is in the optic nerve head region, or is any other ocular feature of interest.

73. An apparatus as claimed in claim 50, wherein said first direction is substantially horizontal.

* * * * *